(12) United States Patent
Tonoike

(10) Patent No.: US 6,767,723 B2
(45) Date of Patent: Jul. 27, 2004

(54) METHOD FOR SYNTHESIS OF NUCLEIC ACIDS

(75) Inventor: Hiroshi Tonoike, Tsukuba (JP)

(73) Assignee: Shimadzu Corporation, Kyoto (JP)

( * ) Notice: Subject to any disclaimer, the term of this patent is extended or adjusted under 35 U.S.C. 154(b) by 140 days.

(21) Appl. No.: 09/818,583

(22) Filed: Mar. 28, 2001

(65) Prior Publication Data

US 2002/0142402 A1 Oct. 3, 2002

(30) Foreign Application Priority Data

Apr. 27, 2000 (JP) ........................................ 2000-127276

(51) Int. Cl.[7] ............................ C12P 19/34; C12Q 1/68; C07G 17/00; C07K 1/00; C07H 21/02
(52) U.S. Cl. ...................... 435/91.1; 435/6; 435/91.2; 435/267; 435/269; 536/23.1; 536/24.3; 536/24.33
(58) Field of Search ........................ 435/6, 91.1, 91.2, 435/267, 269; 536/23.1, 24.3, 24.33

(56) References Cited

U.S. PATENT DOCUMENTS 5,501,963 A * 3/1996 Burckhardt ................. 435/267

OTHER PUBLICATIONS

Steiner et al., "A rapid one–tube genomic DNA extraction process for PCR and RAPD analyses," Nucleic Acids Research, 1995, vol. 23, No. 13, pp. 2569–2570.*
Liu et al., "Effects of three sample preservation methods on total DNA preparation of porcine whole blood," Di–San Junyi Daxue Xuebao, 1999, vol. 21, No. 1, Abstract only.*

* cited by examiner

*Primary Examiner*—Kenneth R. Horlick
*Assistant Examiner*—Young J. Kim
(74) *Attorney, Agent, or Firm*—Rader, Fishman & Grauer PLLC

(57) ABSTRACT

An object of the present invention is to provide a method of treatment and a method of storage that are useful in conducting a nucleic acid synthesis procedure capable of directly amplifying an intended nucleic acid in a living body-derived sample without purification steps.

The present invention provides a method for synthesis of nucleic acids in which a living body-derived sample itself is mixed with a reaction solution for gene amplification and allowed to react, which method comprises treating the sample with a surfactant before the reaction to destruct solid components such as cells or bacterial bodies containing nucleic acids and uniformly disperse them in the sample liquid.

12 Claims, 1 Drawing Sheet

METHOD FOR SYNTHESIS OF NUCLEIC ACIDS

BACKGROUND OF THE INVENTION

1. Field of the Invention

The present invention relates to a method for synthesis of nucleic acids, especially to a method for synthesis of nucleic acids by means of a polymerase chain reaction (hereinafter abbreviated as a PCR).

2. Description of the Related Art

A PCR method is a procedure capable of amplifying an intended DNA fragment as much as several hundred thousand-fold by repeating a process comprised of dissociation of a DNA strand into single strands, binding of primers with sandwiching a particular region of the DNA strand, and a DNA synthesis reaction by the action of a DNA polymerase. The PCR method is described in Japanese Laid-open Patent Publication No.S61-274697 which is an invention by Mullis et al.

A PCR procedure can be used as a highly sensitive method for analyzing nucleic acids in various samples, and particularly it can be used in analysis of nucleic acids in a sample derived from an animal body fluid. The PCR procedure is therefore used for such a purpose of diagnosis or monitoring of an infection, a hereditary disease, and a cancer. The PCR procedure is also suited to DNA typing tests for a transplantation, a paternity test, medical treatments based on an individual genetic information, and the like. For these purposes, a peripheral blood is often selected as a test object.

One drawback of the PCR procedure is that the reaction is inhibited by pigments, proteins, saccharides, or unknown contaminants. Namely, many DNA polymerases including TaqDNA polymerase derived from Thermus aquaticus, a typical thermostable DNA polymerase, are widely known to allow the PCR to be inhibited potently by even a trace amount of living body-derived contaminants existing in the PCR reaction solution. Therefore, the PCR procedure requires a process in which a cell(s), a protozoan (protozoa), a fungus (fungi), a bacterium (bacteria), a virus(es) and the like (hereinafter referred to as a gene inclusion body) are isolated from a subject and then nucleic acids are extracted from the gene inclusion body prior to a DNA amplification. Such process has conventionally been a procedure in which the gene inclusion body is decomposed using an enzyme, a surfactant, a chaotropic agent, or the like, and then nucleic acids are extracted from the decomposed product of the gene inclusion body using, for example, phenol or phenol/chloroform. Recently, an ion-exchange resin, a glass filter, or a reagent having an effect of agglutinating proteins is used in the step of the nucleic acid extraction.

It is difficult, however, to completely remove impurities by purifying nucleic acids in a sample using these procedures, and furthermore, an amount of nucleic acids in a sample recovered by these purification procedures often varies among experiments. For these reasons, a subsequent nucleic acid synthesis may sometimes be unsuccessful, especially when a content of the intended nucleic acid in the sample is low. In addition, these purification procedures involve complicated manipulations and are time-consuming, and there is a high opportunity for contamination during the procedures. Therefore, a simpler, more convenient and effective method of a sample pretreatment is desired in order to solve these problems.

When a body fluid such as blood and a liquid excretion sample such as urine are left to stand, sedimentation of solid components such as cells, bacterial body components and the like occurs to cause heterogeneity in the distribution of cells or bacterial bodies containing an intended nucleic acid. It was therefore necessary to uniformly distribute the solid components in these samples by agitating the samples in advance before the sample addition, when these samples are used for a direct amplification of a nucleic acid.

A peripheral blood is often used, as a test material for a genetic testing. We have hitherto devised methods that provide a nucleic acid synthesis procedure capable of directly amplifying an intended nucleic acid in blood. However, when a whole blood sample is left to stand, sedimentation of blood cells, bacterial body components, or other components occurs to cause heterogeneity in the distribution of blood cells, bacterial bodies, and other components containing the intended nucleic acid. It was therefore necessary to achieve uniform distribution by agitating the sample in advance before its addition, when the blood sample is directly subjected to the PCR. Likewise, the same step was also required when a body fluid and a liquid excretion sample are directly used in the PCR.

SUMMARY OF THE INVENTION

The present inventor invented a process in which a sample is treated with a surfactant, then stored and used without further treatments, as a template for nucleic acid synthesis. The present invention is particularly useful in a method of nucleic acid synthesis in which a body fluid such as blood and a liquid excretion itself such as urine are mixed with a nucleic acid amplification reaction solution and allowed to react, for treating a sample with a surfactant before the reaction and, for example, thereby destructing solid components containing nucleic acids to disperse them uniformly in the sample liquid. In addition, such treatment is expected to have bactericidal, virucidal, and the like effects and thereby reduce the possible risk of infection of a worker caused by a biological sample that is inherent in handling biological samples.

Thus, the present invention is a method for synthesis of nucleic acids to amplify an intended nucleic acid from a sample which comprises homogenizing a living body-derived sample and then directly adding the homogenized sample to a reaction solution to amplify the nucleic acid.

The present invention is the method for synthesis of nucleic acids wherein the sample is homogenized using a surfactant.

The present invention is the method for synthesis of nucleic acids wherein the surfactant is an ionic surfactant.

The present invention is the method for synthesis of nucleic acids wherein the ionic surfactant is an anionic surfactant.

The present invention is the method for synthesis of nucleic acids wherein the anionic surfactant is at least one selected from the group consisting of salts of N-lauroylsarcosine and dodecyl sulfates (e.g. SDS).

The present invention is the method for synthesis of nucleic acids wherein the homogenized sample is subjected to nucleic acid synthesis in a reaction solution containing a nonionic surfactant.

The present invention is the method for synthesis of nucleic acids wherein Tween 20 and/or Nonidet P40 is used as the nonionic surfactant.

Further, the present invention is a method of sample storage, which comprises homogenizing a living body-derived sample and storing the homogenized sample.

According to the present invention, by treating the sample with the surfactant before the reaction, solid components such as cells or bacterial bodies containing nucleic acids can be destructed and uniformly dispersed in the sample liquid, and therefore it is not necessary to agitate the sample in advance for uniformly distributing the solid components in the sample. In addition, the present invention enables long-term sample storage.

DETAILED DESCRIPTION OF THE INVENTION

Figure 1:
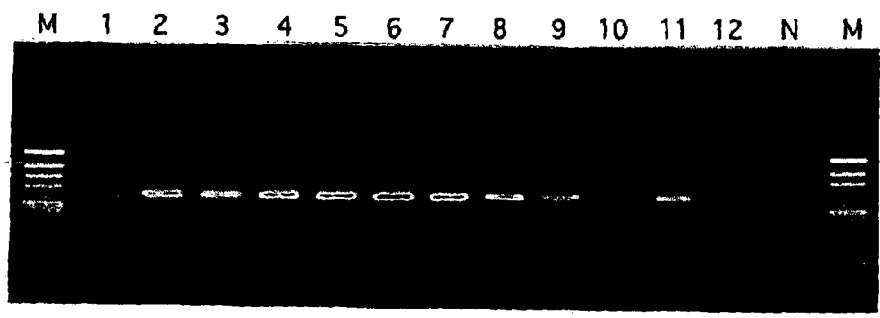
FIG. 1 shows an electrophoretogram of amplified products obtained by the PCR in which a sample treated with a lysis solution was directly added to a PCR reaction solution.

The present invention is a method for synthesis of nucleic acids to amplify an intended nucleic acid from a sample which comprises homogenizing a living body-derived sample and then directly adding the homogenized sample to a reaction solution to amplify the nucleic acid.

As used herein, the term "homogenizing" means a treatment by which nucleic acids are uniformly dispersed in a sample liquid. The term "directly" means no pretreatments other than homogenization is required.

It is preferred to use a surfactant for homogenization. The surfactant includes an anionic surfactant, a cationic surfactant, an amphoteric surfactant, and a nonionic surfactant. When the sample is subjected to nucleic acid amplification within a short period, any of these groups may be adopted. Specific examples of the anionic and the nonionic surfactants are described afterwards. As the cationic surfactant, for example, cetyltrimethylammonium bromide or dodecyltrimethylammonium bromide may be used, and as the amphoteric surfactant, for example, CHAPS, lecithin, lysolecithin, phosphatidylethanolamine, or N-dodecyl-N,N-dimethyl-3-ammonio-1-propane sulfonate may be used.

However, aggregates appear over time and cause heterogeneity in the distribution of nucleic acids in the sample liquid. To solve this problem, the present inventor further investigated and succeeded in avoiding formation of aggregates by using a certain concentration of an anionic surfactant. For example, a blood sample is treated with the anionic surfactant such as dodecyl sulfates (hereinafter collectively referred to as SDS), salts of N-lauroylsarcosine including sodium salt of N-lauroylsarcosine (abbreviated hereinafter to SARKOSYL) and other metallic salts of N-lauroylsarcosine, deoxycholates including sodium deoxycholate and other metallic salts of deoxycholate, or cholates including sodium cholate and other metallic salts of cholate for homogenization. In this treatment, SDS or SARKOSYL is mixed with the sample liquid to attain a concentration of 0.5% or more, preferably about 2%, in order to store the sample for a long period stably in the homogeneous condition.

However, a potent inhibition of the reaction is observed if the PCR is conducted by directly adding a sample treated with the ionic surfactant to a standard reaction solution conventionally used. Therefore, the present inventor further investigated to find a way to suppress the reaction inhibition, and found that this reaction inhibition can be suppressed by using a nonionic surfactant in the reaction. The nonionic surfactant, which maybe used, includes, but not limited to, Nonidet P40, Tween 20, digitonin, n-dodecyl maltoside, octyl glycoside, octyl thioglycoside, Triton X-100, sucrose laurate, and Tethit. Nonidet P40 and/or Tween 20 are used at a concentration each of 0.5% or more, preferably 1 to 5%, in the amplification reaction solution.

The nonionic surfactant may be mixed with the sample liquid homogenized by the ionic surfactant and then added to the reaction solution, or may be added in advance to the reaction solution, and thus the order of addition is not specifically defined.

Furthermore, by homogenizing a sample according to the present invention, it becomes possible to store the sample for a long period. The present invention therefore provides a method of sample storage, which comprises homogenizing a living body-derived sample and storing the homogenized sample. Although a period capable of storing the sample varies depending on the kind of the sample, the kind of the surfactant used for homogenization, concentration, storage condition, and the like, a blood sample can be stored, for example, for several years even at room temperature when treated with the anionic surfactant.

In the present invention, the term "sample" means a gene inclusion body in a living body-derived sample or the living body-derived sample itself, and the term "living body-derived sample" refers to an animal or a plant tissue, a body fluid, an excretion, and the like. The term "gene inclusion body" refers to a cell, a protozoan, a fungus, a bacterium, a virus, and the like. Body fluids include blood, cerebrospinal fluid, milk, and saliva; excretions include feces, urine, and sweat; and cells include leukocytes and platelets, although they are not so limited.

The nucleic acid amplification reaction solution conventionally contains a pH buffer as well as salts such as $MgCl_2$ and KCl, primers, deoxyribonucleotides, and a nucleic acid polymerase. The salts mentioned above may be replaced with other salts as appropriate. In addition, various substances including proteins such as gelatin and albumin and dimethyl sulfoxide are sometimes added.

The pH buffer is prepared by a combination of tris (hydroxymethyl)aminomethane and a mineral acid such as hydrochloric, nitric, or sulfuric acid, and a preferred mineral acid is hydrochloric acid. Alternatively, various other pH buffers, including pH buffers comprising a combination of Tricine, CAPSO (3-N-cyclohexylamino-2-hydroxypropanesulfonic acid), or CHES (2-(cyclohexylamino)ethanesulfonic acid) and caustic soda or caustic potash, may be used. The pH-adjusted buffer is used at a concentration between 10 mM and 100 mM in the nucleic acid amplification reaction solution.

The term "primer" refers to an oligonucleotide that acts as an initiation site of synthesis in the presence of nucleic acids, reagents for amplification and other substances. The primer is desirably single-stranded, and a double-stranded primer may also be used. When the primer is double-stranded, it is desirable to convert it into its single-stranded form prior to the amplification reaction. The primers may be synthesized using known methods, or may be isolated from living organisms.

The term "nucleic acid polymerase" means an enzyme that synthesizes nucleic acids by adding deoxyribonucleotides or a chemical synthesis system doing so. Suitable nucleic acid polymerases include, but not limited to, DNA polymerase I derived from *E.coli,* the Klenow fragment of a DNA polymerase derived from *E.coli,* T4 DNA polymerase, TaqDNA polymerase, T.litoralis DNA polymerase, TthDNA polymerase, PfuDNA polymerase, and a reverse transcriptase.

Furthermore, according to the present invention, pH adjustment of the reaction solution for gene amplification produces a synergistic effect. For example, at a temperature of 25° C., the pH is 8.1 or more, and preferably from 8.5 to 9.5.

In the present invention, polyamines may also be added to the reaction solution for gene amplification.

EXAMPLES

The present invention is further described in the following examples which are not intended to restrict the invention.

Experimental Example 1

A present example describes an experiment in which the PCR was conducted by directly adding a blood sample treated with a final concentration of 2% of SARKOSYL. Human citrated blood was used as the sample. Two microliters of one of lysates having various blood concentrations were directly added to a PCR reaction solution (total volume: 50 μl), and the PCR was conducted. The PCR reaction solution used contained 10 mM Tris-HCl, 50 mM KCl, 1.5 mM MgCl, 200 μM each of dATP, dCTP, dGTP and dTTP, 2.5% Nonidet P40, 0.4 μM each of the primers, and 1.25 units of Taq DNA polymerase (TaKaRa Taq: Takara Shuzo, Kyoto, Japan).

The PCR primers were oligonucleotides having a nucleotide sequence of the plus strand (SEQ ID. NO. 1) or the minus strand (SEQ ID. NO. 2) located within the human beta-globin coding region, and these primers may produce 408 bp of an amplification product by the PCR (Saiki, R. K., Gelfand, D. H., Stoffel, S., Scharf, S. J., Higuchi, R., Horn, G. T., Mullis, K. B. and Erlich, H. A. (1988) Science 239, 487–491).

5'GAAGAGCCAAGGACAGGTAC 3'

5'GGAAAATAGACCAATAGGCAG 3'.

The PCR involved a preheating at 94° C. for 4.5 minutes, 40 cycles each of which consists 1 minute at 94° C. followed by 1 minute at 55° C. followed by 1 minute at 72° C., and then the final polymerization at 72° C. for 7 minutes. After the completion of the PCR, 5 μl of the reaction solution was subjected to an electrophoresis on a 2.5% agarose gel in TAE (40 mM Tris-acetate, 1 mM EDTA, pH 8.0) containing 0.5 μg/ml ethidium bromide to detect the amplification products.

FIG. 1 shows the electrophoretogram of PCR products obtained by the PCR in which the sample treated with the lysis solution was directly added to the PCR reaction solution.

In the figure, a lane M indicates molecular weight makers; a lane 1 indicates the result obtained with the lysate of which blood content was ½; a lane 2 indicates the result obtained with the lysate of which blood content was ¼; and lanes 3–12 similarly indicate the results obtained with the lysates of which blood contents were 2-fold serially diluted ones in the order. A lane N indicates the result obtained by adding 2% SARKOSYL solution containing no blood.

It can be seen from the figure that the PCR product could be detected stably and strongly in the lanes 1–12.

Experimental Example 2

Figure 2:
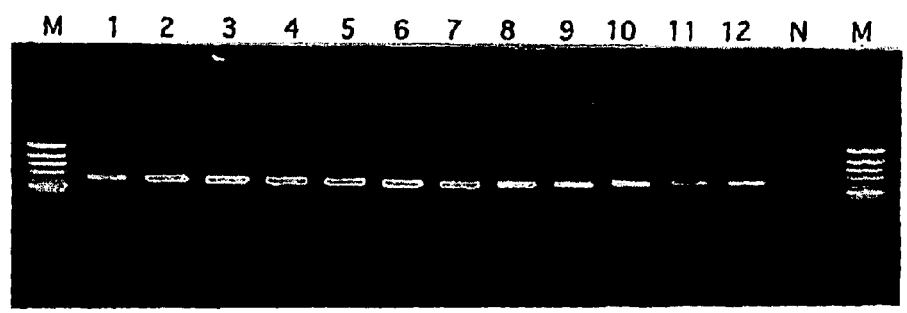
FIG. 2 shows an electrophoretogram of amplified products obtained by the PCR in which a sample treated with a lysis solution was stored for a long period and then directly added to a PCR reaction solution.

This example describes an experiment in which a blood sample was treated with a final concentration of 2% of SARKOSYL, stored for 10 months at room temperature, and then directly added to a reaction solution to conduct the PCR. Human citrated blood was used as the blood sample. Two microliters of one of lysates having various blood concentrations were directly added to a PCR reaction solution (total volume: 50 μl), and the PCR was conducted. The composition of the PCR reaction solution, conditions for the PCR and for the electrophoresis after the PCR were the same as in Experimental Example 1. The electrophoretogram is shown in FIG. 2.

In the figure, a lane M indicates molecular weight makers; a lane 1 indicates the result obtained with a lysate of which blood content was ½; a lane 2 indicates the result obtained with the lysate of which blood content was ¼; and lanes 3–12 similarly indicate the results obtained with the lysates of which blood contents were 2-fold serially diluted ones in the order. A lane N indicates the result obtained by adding 2% SARKOSYL solution containing no blood.

It can be seen from the figure that the PCR product could be detected stably and strongly as same as in FIG. 1 even when the samples had been stored for a long period after the lysis treatment.

Although the nonionic surfactant was used in this example, it is not mecessarily essential to use the nonionic surfactant, since the PCR can be stably achieved in the absence of nonionic surfactant if the amount of a blood lysate added to the PCR reaction solution is reduced.

What is claimed is:

1. A method for synthesis of nucleic acids to amplify an intended nucleic acid from a sample which comprises:

homogenizing a living body-derived sample to produce a homogenized sample consisting essentially of said living body-derived sample and a surfactant; and then directly adding the homogenized sample to a PCR reaction solution to amplify the nucleic acid.

2. The method for synthesis of nucleic acids according to claim 1, wherein the sample is homogenized using a surfactant.

3. The method for synthesis of nucleic acids according to claim 2, wherein the surfactant is an ionic surfactant.

4. The method for synthesis of nucleic acids according to claim 3, wherein the ionic surfactant is an anionic surfactant.

5. The method for synthesis of nucleic acids according to claim 4, wherein the anionic surfactant is at least one selected from the group consisting of salts of N-lauroylsarcosine and dodecyl sulfates (e.g. SDS).

6. The method for synthesis of nucleic acids according to claim 5, wherein a concentration of the salt of N-lauroylsarcosine and/or dodecyl sulfate is 0.5 wt % or more in a sample liquid.

7. The method for synthesis of nucleic acids according to claim 1, wherein the sample is a gene inclusion body in the living body-derived sample, or the living body-derived sample itself.

8. A method for synthesis of nucleic acids to amplify an intended nucleic acid from a sample which comprises:

homogenizing a living body-derived sample to produce a homogenized sample consisting essentially of said living body-derived sample and a surfactant; and then directly adding the homogenized sample to a PCR reaction solution to amplify the nucleic acid;

wherein the homogenized sample is subjected to nucleic acid synthesis in a reaction solution containing a nonionic surfactant.

9. The method for synthesis of nucleic acids according to claim 8, wherein one or more sorts of nonionic surfactants are used as the nonionic surfactant.

10. The method for synthesis of nucleic acids according to claim 9, wherein Tween 20 and/or Nonidet P40 is used as the nonionic surfactant.

11. The method for synthesis of nucleic acids according to claim 10, wherein a concentration of Nonidet P40 and/or Tween 20 is 0.5 wt % or more in the reaction solution.

12. The method for synthesis of nucleic acids according to claim 7, which further comprises storing said homogenized sample (1) after homogenizing said living body-derived sample and (2) before adding said homogenized sample to the PCR reaction solution.

* * * * *

SEQUENCE LISTING

<160> NUMBER OF SEQ ID NOS: 2

<210> SEQ ID NO 1
<211> LENGTH: 20
<212> TYPE: DNA
<213> ORGANISM: artificial sequence
<220> FEATURE:
<223> OTHER INFORMATION: primer

<400> SEQUENCE: 1
gaagagccaa ggacaggtac            20

<210> SEQ ID NO 2

```
-continued

<211> LENGTH: 21
<212> TYPE: DNA
<213> ORGANISM: artificial sequence
<220> FEATURE:
<223> OTHER INFORMATION: primer

<400> SEQUENCE: 2
ggaaaataga ccaataggca g                                              21
```